(12) United States Patent
Mitch (10) Patent No.: US 9,937,466 B2
(45) Date of Patent: Apr. 10, 2018

(54) ULTRAVIOLET AND HYDROGEN PEROXIDE OR OZONE OR OZONE AND HYDROGEN PEROXIDE TREATMENT TO SIMULTANEOUSLY CONTROL NITROSAMINE, NITRAMINE, AMINE AND ALDEHYDE EMISSIONS FROM AMINE-BASED CARBON CAPTURE

(75) Inventor: William A. Mitch, Hamden, CT (US)

(73) Assignee: Yale University, New Haven, CT (US)

( * ) Notice: Subject to any disclaimer, the term of this patent is extended or adjusted under 35 U.S.C. 154(b) by 1107 days.

(21) Appl. No.: 14/001,247

(22) PCT Filed: Feb. 23, 2012

(86) PCT No.: PCT/US2012/026309
§ 371 (c)(1),
(2), (4) Date: Jan. 29, 2014

(87) PCT Pub. No.: WO2012/116171
PCT Pub. Date: Aug. 30, 2012

(65) Prior Publication Data
US 2014/0163299 A1    Jun. 12, 2014

Related U.S. Application Data

(60) Provisional application No. 61/445,652, filed on Feb. 23, 2011.

(51) Int. Cl.
*B01D 53/75* (2006.01)
*B01D 53/00* (2006.01)
(Continued)

(52) U.S. Cl.
CPC ............... *B01D 53/75* (2013.01); *A61L 9/20* (2013.01); *B01D 53/007* (2013.01); *B01D 53/44* (2013.01);
(Continued)

(58) Field of Classification Search
CPC .. B01D 53/75; B01D 2251/104; B01D 53/54; B01D 53/1425; B01D 2251/106;
(Continued)

(56) References Cited

U.S. PATENT DOCUMENTS

| | | | |
|---|---|---|---|
| 5,087,374 A * | 2/1992 | Ding | A62D 3/13 134/1 |
| 5,587,069 A | 12/1996 | Downey, Jr. | |

(Continued)

OTHER PUBLICATIONS

Getoff, et al., Pulse Radiolysis of Oxalic Acid and Oxalates, Journal of Physical Chemistry,, 75, 6, pp. 749-755, 1971.
(Continued)

*Primary Examiner* — Walter D. Griffin
*Assistant Examiner* — Cameron J Allen
(74) *Attorney, Agent, or Firm* — McCarter & English, LLP (57) ABSTRACT

Apparatuses for controlling emissions of carbon capture facilities and associated methods are disclosed that generally involve a chamber defining at least one washwater packing. The exemplary apparatuses further include at least one washwater return line, a UV treatment zone and a hydrogen peroxide treatment zone. The UV treatment zone generally receives UV energy sufficient to substantially destroy a first emission compound and the hydrogen peroxide treatment zone generally receives a hydrogen peroxide medium sufficient to substantially oxidize a second emission compound to a less volatile final product. An alternative exemplary apparatus generally involves a UV treatment zone and an ozonation treatment zone, further including a hydrogen peroxide treatment zone applied within the ozonation treatment zone. The exemplary methods generally include applying at least one of a UV treatment, a hydrogen peroxide treatment and an ozonation treatment.

10 Claims, 7 Drawing Sheets

(51) Int. Cl.
  *B01D 53/44* (2006.01)
  *B01D 53/54* (2006.01)
  *A61L 9/20* (2006.01)
  *B01D 53/14* (2006.01)

(52) U.S. Cl.
  CPC .......... *B01D 53/54* (2013.01); *B01D 53/1425* (2013.01); *B01D 2251/104* (2013.01); *B01D 2251/106* (2013.01); *B01D 2257/704* (2013.01); *B01D 2259/804* (2013.01)

(58) Field of Classification Search
  CPC ........... B01D 2257/704; B01D 53/007; B01D 2259/804; B01D 53/44; A61L 9/20
  See application file for complete search history.

(56) References Cited

U.S. PATENT DOCUMENTS

| | | | |
|---|---|---|---|
| 5,837,148 | A | 11/1998 | Danzmann et al. |
| 5,935,525 | A | 8/1999 | Lincoln et al. |
| 6,632,659 | B1 * | 10/2003 | Den .................. B01D 53/8668 435/121 |
| 2008/0250715 | A1 * | 10/2008 | Cooper .................. B01D 47/06 48/197 FM |

OTHER PUBLICATIONS

Willson, et al. The Standardization of Hydroxyl Radical Rate Data From Radiation Chemistry, International Journal of Radiat. Phys. Chem., 3, p. 211-220, 1971.
Kuz'min, Reactions of the $CO_3$ and $SIO_3$ Radical Anions, High Energy Chemistry, 6, 4, pp. 338-339, 1972.
Keefer, et al., N-Nitrosation by Nitrite Ion in Neutral and Basic Medium, Science, 181, pp. 1245-1247, 1973.
Mirivish, Formation of N-Nitroso Compounds: Chemistry, Kinetics, and in Vivo Occurrence, Toxicology and Applied Pharmacology, 31, pp. 325-351, 1975.
Zepp, Quantum Yields for Reaction of Pollutants in Dilute Aqueous Solution, Environmental Science Technology, 12, 3, pp. 327-329, 1978.
Casado, et al., Nitrite Ion as a Nitrosating Reagent, Nitrosation of Morpholine and Diethylamine in the Presence of Formaldehyde, Journal of the Chemical Society-Perkin Transaction 2, 12, pp. 1963-1966, 1984.
Pryor, et al., Kinetics of Ozonation, 2. Amino Acids and Model Compounds in Water and Comparisons to Rates in Nonpolar Solvents, Journal of Am. Chemical Society, 106, pp. 7094-7100, 1984.
Elango, et al., Reactions of the Carbonate Radical With Aliphatic Amines, Tetrahedron, 41, 18, pp. 3837-3843, 1985.
Schuchmann, et al., The Rapid Hydration of the Acetyl Radical. A Pulse Radiolysis Study of Acetaldehyde in Aqueous Solution, Journal of Am. Chemical Society, 110, pp. 5698-5701, 1988.
Draganic, et al., Radiolysis of Aqueous Solutions of Ammonium Bicarbonate Over A Large Dose Range, Radiat. Phys. Chem., 38, 3, pp. 317-321, 1991.
Huie et al., Temperature Dependence of the Rate Constants for Reactions of the Carbonate Radical with Organic and Inorganic Reductants, International Journal of Chemical Kinetics, 23, pp. 541-552, 1991.
Motohashi, et al., Competitive Measurement of Rate Constants for Hydroxyl Radical Reactions Using Radiolytic Hydroxylation of Benzoate, Chem. Pharm. Bull, 41, 10, pp. 1842-1845, 1993.
Chin, et al., A Temperature-Dependent Competitive Kinetics Study of the Aqueous-Phase Reactions of OH Radicals with Formate, Formic Acid, Acetate, Acetic Acid, and Hydrated Formaldehyde, Aquatic and Surface Photochemistry, CRC Press, Boca Raton, pp. 85-96, 1994.
Crittenden, et al., A Kinetic Model For $H_2O_2$/UV Process in a Completely Mixed Batch Reactor, Water Research, 33, 10, pp. 2315-2328, 1999.
Levenspiel, Chapter 3: Interpretation of Batch Reactor Dta, Chemical Reaction Engineering, John Wiley & Sons, New York, pp. 65-67, 1999.
Mack, et al., Photochemistry of Nitrite and Nitrate in Aqueous Solution: A Review, Journal of Photochemistry and Photobiology A: Chemistry, 128, pp. 1-13, 1999.
Winkelman, et al., Kinetics and Chemical Equilibrium of the Hydration of Formaldehyde, Chemical Engineering Science, 57, pp. 4067-4076, 2002.
Von Gunten, Ozonation of Drinking Water: Part I. Oxidation Kinetics and Product Formation, Water Research, 37, pp. 1443-1467, 2003.
Lee, et al., UV Photolytic Mechanism of N-Nitrosodimethylamine in Water: Roles of Dissolved Oxygen and Solution pH, Environmental Science Technology, 39, pp. 9702-9709, 2005.
Kishore, et al., OH Radical Reactions With Ethanolamines: Formation of Reducing as Well as Oxidaizing Radicals, Res. Chem. Intermed., 31, 9, pp. 875-884, 2005.
Kulshrestha et al., Application of an Optimized Totall N-Nitrosamine (TONO) Assay to Pools: Placing N-Nitrosodimethylamine (NDMA) Determinations into Perspective, Environmental Science Technology, 44, pp. 3369-3375, 2010.
PCT/US2012/026309, Feb. 23, 2012, WO 2012/116171.
PCT International Search Report and Written Opinion from dated Aug. 3, 2012.

* cited by examiner

ULTRAVIOLET AND HYDROGEN PEROXIDE OR OZONE OR OZONE AND HYDROGEN PEROXIDE TREATMENT TO SIMULTANEOUSLY CONTROL NITROSAMINE, NITRAMINE, AMINE AND ALDEHYDE EMISSIONS FROM AMINE-BASED CARBON CAPTURE

CROSS-REFERENCE TO RELATED APPLICATIONS

This application is based on and claims the priority benefit of U.S. Provisional Application No. 61/445,652, filed Feb. 23, 2011. The entire content of the foregoing provisional patent application is incorporated herein by reference.

BACKGROUND

Technical Field

The present disclosure is directed to an apparatus and method of treatment of contaminant emissions from carbon capture facilities and, in particular, to an improved apparatus and method of simultaneously controlling and/or treating emissions of amines, nitrosamines, nitramines and aldehydes from flue gases in a cost efficient and/or effective manner.

Background Art

In general, contaminant emissions from carbon capture facilities are of great concern in the industry due to their potential hazardous effect on the environment and/or humans. There are currently no standard carbon capture exhaust gas treatments for, e.g., nitrosamines, nitramines, and the like, and those for amines generally rely on, for example, washwater scrubbers employing pH adjustment of washwater and/or higher washwater replacement rates. The concentrations of contaminants in washwater provide one of the best estimates of contaminant emissions from carbon capture facilities to downwind communities. Systems generally configured as scrubbers designed to remove contaminants from the flue gas currently exist. However, contaminants typically accumulate in the washwater, thus reducing the driving force for mass transfer from the flue gas to the washwater. Additionally, for contaminants that form in the washwater, the mass transfer driving force can work in the opposite direction, such that the washwater would serve as a source of contaminants to the exhaust gas as it is recirculated through the system.

Contaminants of particular concern that generally accumulate in washwater include, e.g., nitrosamines, nitramines, amines, aldehydes, nitrite, and the like. Nitrosamines, nitramines and aldehydes are generally of specific concern due to their potential direct toxicity. Amines are of concern due to their potential to form toxic products downwind. In addition, even at an alkaline pH, aldehydes can catalyze the nitrosation of amines by nitrite. Accordingly, the accumulation of these products in the washwater may foster nitrosamine formation, such that the washwater serves as a source of nitrosamines to the exhaust gas.

Another important N-nitrosamine formation pathway involves nitrite, i.e., a nitrosation pathway relevant to washwaters. Under acidic conditions, formation of the nitrosating agent, e.g., $N_2O_3$, generally occurs in a reaction that is second order in nitrite as shown below in Equation 1 (see, e.g., Mirvish, S. S., *Toxicology and Applied Pharmacology*, 31, p. 325-351 (1975)).

$$2NO_2^- + 3H^+ \rightarrow N_2O_3 + H_2O + H^+ \quad (1)$$

However, aldehydes have been found to catalyze nitrosation by nitrite, thereby enabling significant formation at neutral and alkaline pH (see, e.g., Keefer, L. K. et al., *Science*, 181, p. 1245-1247 (1973)). For example, as shown in Equation 2 below, a reaction between dimethylamine and formaldehyde forms a carbinolamine (see, e.g., Casado, J. et al., *Journal of the Chemical Society-Perkin Transaction* 2, 12, p. 1963-1966 (1984)). With reference to Equation 3, protonation of the carbinolamine, followed by dehydration, generally forms an iminium ion. The iminium ion further generally reacts with nitrite to form a nitrosamine, as illustrated by Equation 4, thereby releasing formaldehyde for further reactions.

$$(CH_3)_2NH + CH_2O \rightarrow (CH_3)_2NCH_2OH \quad (2)$$

$$(CH_3)_2NCH_2OH + H^+ \rightarrow (CH_3)_2N^+NCH_2OH \rightarrow (CH_3)_2N^+ = CH_2 + H_2O \quad (3)$$

$$(CH_3)_2N^+ = CH_2 + NO_2^- \rightarrow (CH_3)_2N-N=O + CH_2O \quad (4)$$

Due to the high concentrations of aldehydes anticipated to be present in the absorbent solution and/or in the washwater, and because nitrite generally occurs in washwater, the nitrosation pathway is likely to be a significant pathway for nitrosamine formation.

Figure 1:
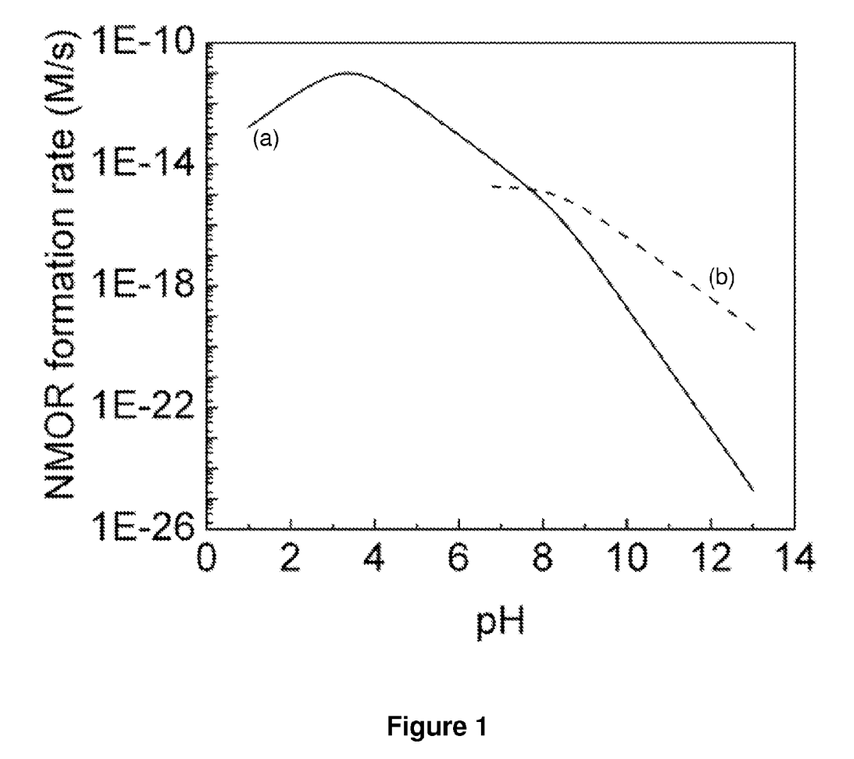
FIG. 1 shows the modeled N-nitrosomorpholine formation from 100 μM morpholine and 400 μM nitrite in (a) the absence or (b) presence of 100 μM formaldehyde.

Turning now to FIG. 1, modeled nitrosation rates (M/s) of about 100 μM morpholine by about 400 μM nitrite in the absence (line "a") and/or presence (line "b") of about 100 μM formaldehyde as a function of pH are presented (see, e.g., Mirvish, S. S., *Toxicology and Applied Pharmacology*, 31, p. 325-351 (1975)). Nitrosation of alkylamines by acid-catalyzed nitrosation in the absence of aldehydes is generally maximized at a pH of about 3 to 4. Catalysis of nitrosation by formaldehyde further generally increased nitrosation rates by about four orders of magnitude near a pH of about 10, typical of washwaters.

There are currently two options being pursued in the industry to increase the driving force for transfer of amines from the exhaust gas to the washwater. The first option generally involves the addition of sequential washwater sections. In particular, increasing the number of sequential washwater sections is generally equivalent to increasing the number of transfer units in a plug flow reactor, thereby increasing the removal efficiency of amines. In addition, since nitrosamines and nitramines are typically water soluble, partial removal of nitrosamines and nitramines should also be expected. However, the cost of adding sequential washwater sections is substantially high. Further, these improvements may be temporary, as the accumulation of amines in the washwater generally continues to reduce the mass transfer driving force and reactions of residual $NO_x$ with amines in the washwater to form nitrosamines and/or nitramines would cause the washwater to serve as a source of nitrosamines to the exhaust gas.

The second option currently being pursued in the industry generally involves reducing the pH in a single washwater section. In particular, without pH adjustment, most washwaters generally achieve a pH of about 10.5, which is above the dissociation constant $pK_a$ (hereinafter "$pK_a$") of most amines. Reducing the pH below the $pK_a$ of amines can significantly reduce their volatility, as the charged forms of amines are non-volatile. Although amines can still accumulate to reach Henry's law equilibrium with the flue gas, a substantial mass of amines could be stored in the washwater in their charged forms. However, upon reaching Henry's law equilibrium, the washwater generally no longer serves as an amine sink. Further, the $pK_a$ values for nitrosamines are significantly lower than for amines. Therefore, only at the lowest pH values will acidification aid nitrosamine removal. Additionally, the low pH environment generally promotes the nitrosation of amines by nitrite, thereby permitting the washwater to become a source of nitrosamines.

Both of these options generally rely on phase transfer to reduce losses by storing compounds in the washwater. Therefore, in both cases, the accumulation of the products over time generally reduces the driving force for contaminant removal. Additionally, disposal of washwaters containing these accumulated contaminants is problematic, as the washwaters may be considered hazardous waste.

Thus, a need exists for improved apparatuses and methods of treatment of contaminant emissions from carbon capture facilities. In particular, a need exists for improved apparatuses and methods of simultaneously controlling and/or treating emissions of amines, aldehydes, nitrosamines and nitramines from flue gases in a cost efficient and/or effective manner, and for destroying these contaminants to facilitate the safe disposal of the used washwaters.

These and other needs are addressed by the exemplary apparatuses and methods of the present disclosure.

SUMMARY

In accordance with embodiments of the present disclosure, an exemplary apparatus or system for controlling and/or treating emissions of carbon capture facilities and destroying contaminants within washwaters is provided. In particular, the exemplary apparatus or system generally includes a chamber defining at least one washwater packing zone positioned therewithin. The exemplary apparatus or system further includes at least one washwater return line, an ultraviolet treatment zone (hereinafter "UV treatment zone") and a hydrogen peroxide treatment zone. The UV treatment zone generally includes a first UV treatment and a second UV treatment. The UV treatment zone generally receives UV energy sufficient to destroy and/or substantially destroy a first emission compound, including at least one of a nitrosamine and a nitramine. Further, the first and second UV treatments can be applied in at least one of a water phase and a gas phase. The first UV treatment can be applied above and/or below the at least one washwater packing zone. The second UV treatment can be applied to the at least one washwater return line.

The hydrogen peroxide treatment zone generally includes a hydrogen peroxide injection applied within the second UV treatment. The hydrogen peroxide treatment zone receives a hydrogen peroxide medium sufficient to oxidize and/or substantially oxidize a second emission compound to a less volatile final product. In particular, the hydrogen peroxide addition within the confines of the second UV treatment unit produces radicals (e.g., hydroxyl radicals as well as carbonate radicals produced from hydroxyl radical reactions with carbonates) that oxidize and/or substantially oxidize a second emission compound to final products that are less volatile compounds that are not readily nitrosated and/or nitrated, e.g., less volatile ionic compounds, non-volatile ionic compounds, and the like. The second emission compound generally includes at least one of a nitrite, an aldehyde and an amine, and the final products generally include at least one of a nitrate, a carboxylic acid, and various oxidized products of amines. Further, the combined first UV, second UV and hydrogen peroxide treatment zone generally inhibits and/or substantially inhibits nitrosamine formation.

In accordance with another embodiment of the present disclosure, an alternative exemplary apparatus or system for controlling and/or treating emissions of carbon capture facilities and destroying contaminants within washwaters is provided. In particular, the exemplary apparatus or system generally includes a chamber defining at least one washwater packing zone positioned therewithin. The exemplary apparatus or system further includes at least one washwater return line, a UV treatment zone and an ozonation treatment zone. The UV treatment zone generally includes a first UV treatment and a second UV treatment. The UV treatment zone generally receives UV energy sufficient to destroy and/or substantially destroy a first emission compound, including at least one of a nitrosamine and nitramine. Further, the first and second UV treatments can be applied in at least one of a water phase and a gas phase. The first UV treatment can be applied above and/or below the at least one washwater packing zone. The second UV treatment can be applied to the at least one washwater return line.

The ozonation treatment zone generally includes an ozone injection applied to the at least one washwater return line which is sufficient to oxidize and/or substantially oxidize a second emission compound to final products that are less volatile compounds that are not readily nitrosated and/or nitrated, e.g., less volatile ionic compounds, non-volatile ionic compounds, and the like. The second emission compound generally includes at least one of a nitrite, an aldehyde and an amine, and the final products generally include at least one of a nitrate, a carboxylic acid and various oxidized products of amines. The exemplary ozonation treatment zone can further include a hydrogen peroxide treatment within the ozonation treatment zone. The hydrogen peroxide treatment can be a hydrogen peroxide injection which oxidizes and/or substantially oxidizes a second emission compound to final products that are less volatile compounds that are not readily nitrosated and/or nitrated. Further, the ozonation treatment, the hydrogen peroxide treatment, or a combination of the above as discussed herein, generally inhibit and/or substantially inhibit nitrosamine formation. Applying and/or introducing the ozonation treatment zone at a beginning portion of the at least one washwater return line minimizes an ozone loss in an exhaust gas.

In accordance with further embodiments of the present disclosure, an exemplary method for controlling and/or treating emissions of carbon capture facilities and destroying contaminants within washwaters is provided. In particular, the exemplary method generally includes providing at least one washwater packing and at least one washwater return line, applying a UV treatment and applying a hydrogen peroxide treatment. The UV treatment generally includes a first UV treatment and a second UV treatment. The UV treatment generally destroys and/or substantially destroys a first emission compound, including at least one of a nitrosamine and a nitramine. The UV treatment can further be applied in at least one of a water phase and a gas phase. The first UV treatment can be applied at least at one of above and below the at least one washwater packing. The second UV treatment can be applied to the at least one washwater return line. The hydrogen peroxide treatment can be a hydrogen peroxide injection within the second UV treatment.

In accordance with another embodiment of the present disclosure, an alternative exemplary method for controlling and/or treating emissions of carbon capture facilities and destroying contaminants within washwaters is provided. In particular, the exemplary method generally includes providing at least one washwater packing and at least one washwater return line, applying a UV treatment and applying an ozonation treatment. The UV treatment generally includes a first UV treatment and a second UV treatment. The UV treatment generally destroys and/or substantially destroys a first emission compound, including at least one of a nitrosamine and a nitramine. The UV treatment can further be applied in at least one of a water phase and a gas phase. The first UV treatment can be applied at least at one of above and below the at least one washwater packing. The second UV treatment can be applied to the at least one washwater return line.

The exemplary ozonation treatment can include applying an ozone injection to the at least one washwater return line. The ozonation treatment generally oxidizes and/or substantially oxidizes a second emission compound to a less volatile final product and can be applied at a beginning portion of the at least one washwater return line to minimize an ozone loss in the exhaust gas. The second emission compound generally includes at least one of a nitrite, an aldehyde and an amine, and the final products generally include at least one of a nitrate, a carboxylic acid, and various oxidized products of amines. Further, the ozonation treatment generally inhibits and/or substantially inhibits nitrosamine formation in the at least one washwater return line.

The step of applying the ozonation treatment can further include applying a hydrogen peroxide treatment within the ozonation treatment. The hydrogen peroxide treatment can be a hydrogen peroxide injection. The addition of hydrogen peroxide to the ozonation treatment step further promotes the formation of radicals (e.g., hydroxyl radicals as well as carbonate radicals produced from hydroxyl radical reactions with carbonates) that oxidize and/or substantially oxidizes a second emission compound to a less volatile final product. The second emission compound generally includes at least one of a nitrite, an aldehyde and an amine, and the final products generally include at least one of a nitrate, a carboxylic acid and various oxidized products of amines. Further, the ozonation treatment combined with hydrogen peroxide generally inhibits and/or substantially inhibits nitrosamine formation in the at least one washwater return line.

Additional features, functions and benefits associated with the disclosed apparatus for controlling emissions and associated methods will be apparent from the detailed description which follows.

BRIEF DESCRIPTION OF THE DRAWINGS

For a fuller understanding of the present disclosure, reference is made to the following description taken in connection with the accompanying drawings, in which.

DESCRIPTION OF EXEMPLARY EMBODIMENT(S)

In accordance with embodiments of the present disclosure, an exemplary apparatus or system for controlling and/or treating emissions of carbon capture facilities and destroying contaminants within washwaters is provided. In particular, the exemplary apparatus or system generally includes a chamber defining at least one washwater packing zone positioned therewithin. The exemplary apparatus or system further includes at least one washwater return line, a UV treatment zone and a hydrogen peroxide treatment zone. The UV treatment zone generally includes a first UV treatment and a second UV treatment. The UV treatment zone generally receives UV energy sufficient to destroy and/or substantially destroy a first emission compound, including at least one of a nitrosamine and a nitramine. Further, the first and second UV treatments can be applied in at least one of a water phase and a gas phase. The first UV treatment can be applied above and/or below the at least one washwater packing zone. The second UV treatment can be applied to the at least one washwater return line.

In accordance with another embodiment of the present disclosure, an alternative exemplary apparatus or system for controlling and/or treating emissions of carbon capture facilities and destroying contaminants within washwaters is provided. In particular, the exemplary apparatus or system generally includes a chamber defining at least one washwater packing zone positioned therewithin. The exemplary apparatus or system further includes at least one washwater return line, a UV treatment zone and an ozonation treatment zone. The UV treatment zone generally includes a first UV treatment and a second UV treatment. The UV treatment zone generally receives UV energy sufficient to destroy and/or substantially destroy a first emission compound, including at least one of a nitrosamine and nitramine. Further, the first and second UV treatments can be applied in at least one of a water phase and a gas phase. The first UV treatment can be applied above and/or below the at least one washwater packing zone. The second UV treatment can be applied to the at least one washwater return line.

The exemplary apparatuses or systems and methods disclosed herein are generally directed to destroying and/or substantially destroying emission compounds, e.g., amines, nitrosamines, nitramines, aldehydes and the like, continuously within the washwater and converting said emission compounds to less volatile products and/or compounds. The continuous destruction of emission compounds, e.g., first and second emission compounds, can generally maintain a low steady-state concentration of said compounds, thereby allowing the driving force for contaminant removal by phase transfer to be maintained without pH adjustment over prolonged cycles/runs. The destruction of emission compounds generally includes a combination of two treatments, i.e., the UV treatment for direct photolytic destruction of first emission compounds, and either the addition of hydrogen peroxide within the UV treatment to generate radicals, the ozonation treatment, or the addition of hydrogen peroxide within the ozonation treatment to oxidize and/or substantially oxidize second emission compounds (FIGS. 2(a)-(c)).

1. UV and Hydrogen Peroxide Treatment

Figure 2A:
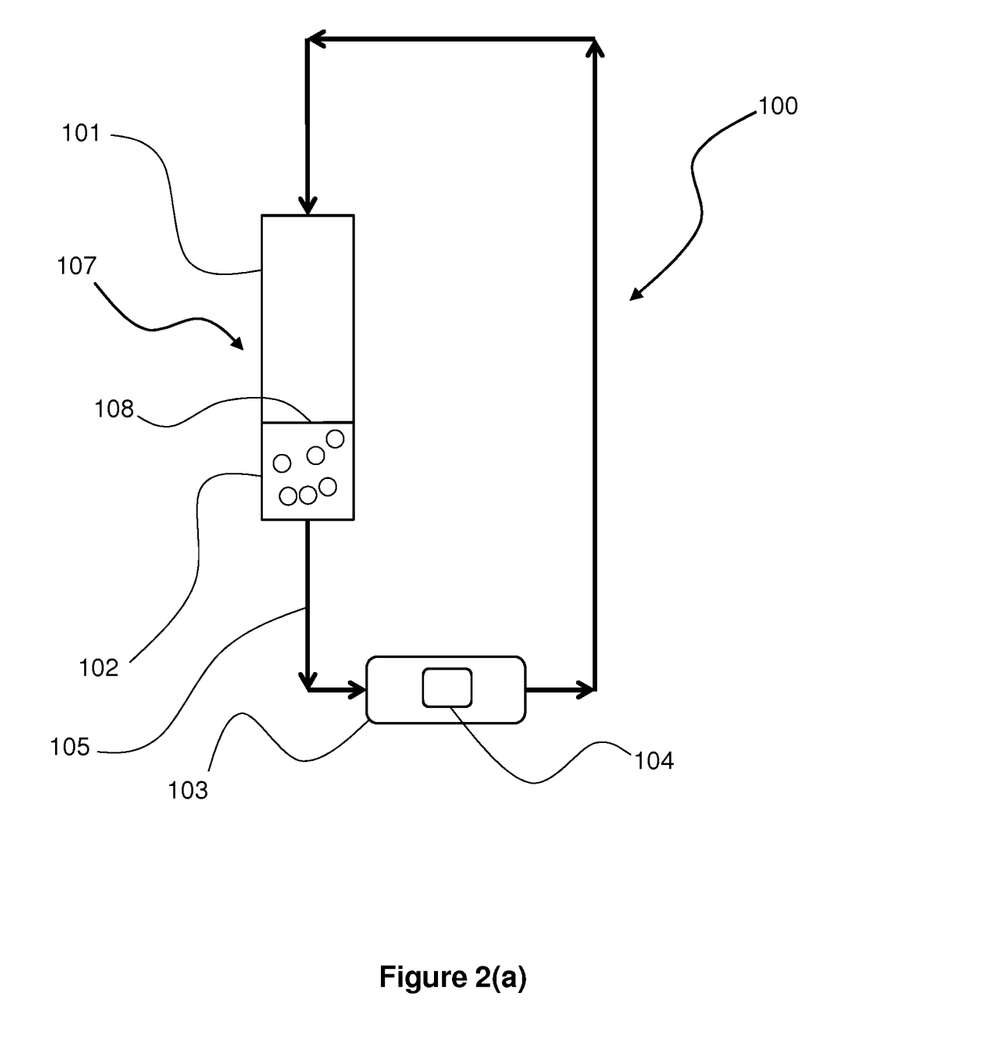
FIGS. 2(a)-(c) are block diagrams of exemplary embodiments of an apparatus for controlling emissions of carbon capture facilities according to the present disclosure.
Figure 2B:
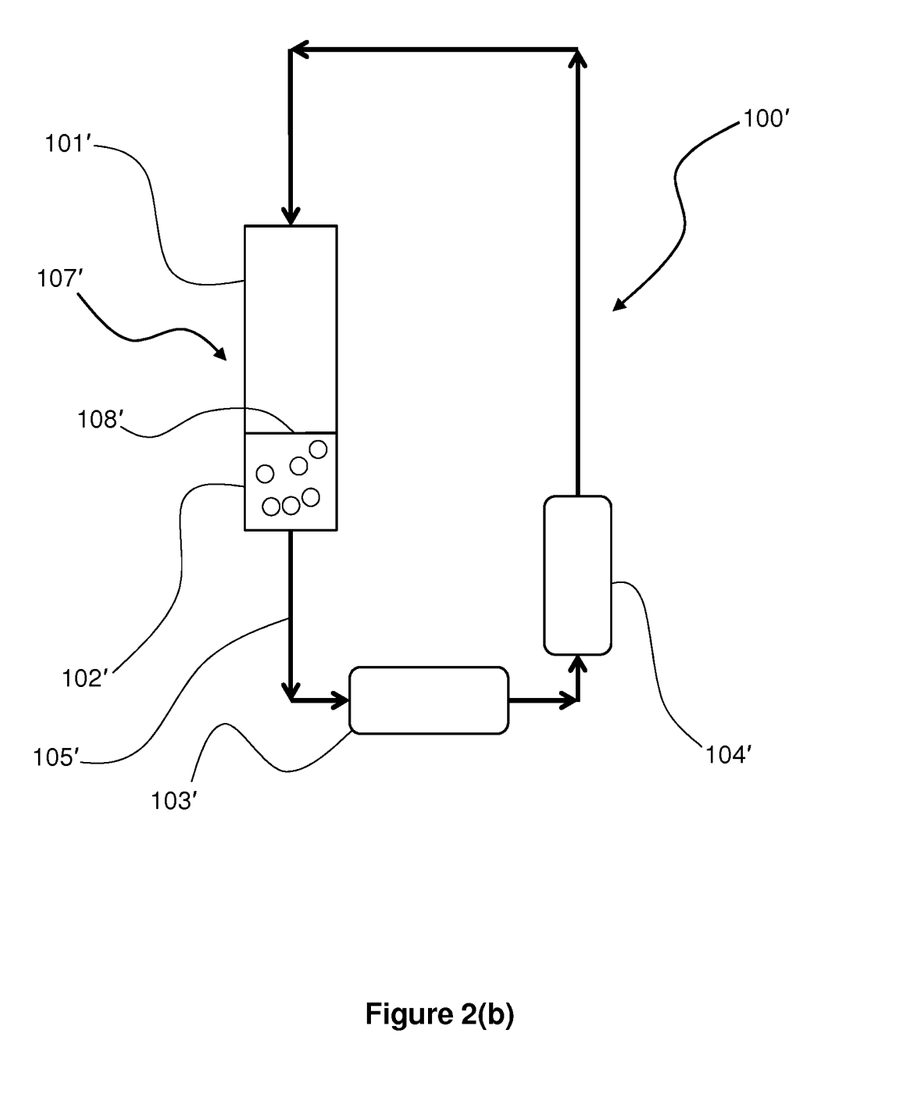
Figure 2C:
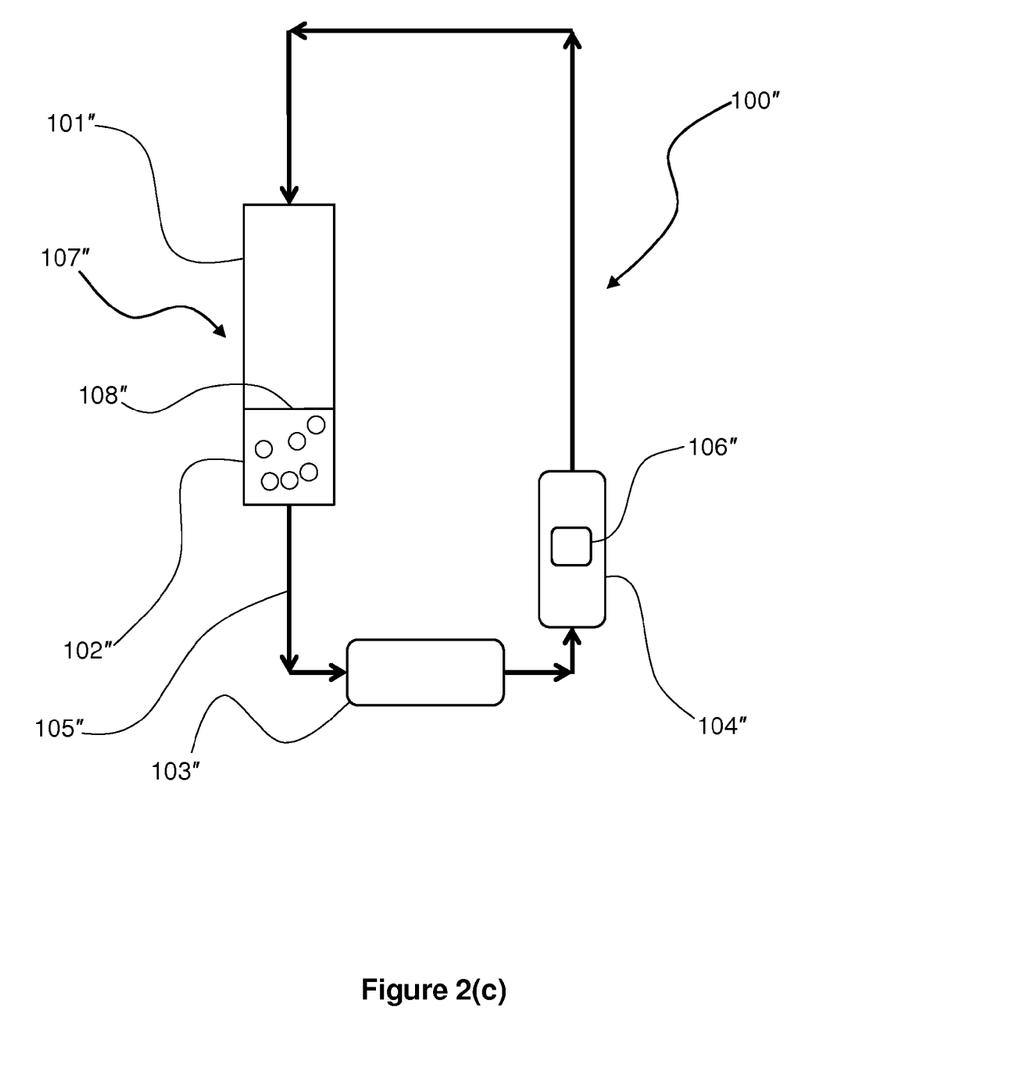

Turning now to FIGS. 2(a)-(c), the exemplary apparatuses or systems for controlling emissions of carbon capture facilities (hereinafter "apparatus") are provided. In particular, the exemplary apparatus 100 of FIG. 2(a) generally includes a chamber 107 defining at least one washwater packing zone 101 positioned therewithin. The chamber 107 can be, e.g., a pipeline, and the like. The exemplary apparatus 100 further includes a first UV treatment 102 applied to an area below the washwater packing zone 101, a washwater return line 105, a second UV treatment 103, e.g., a UV illumination system, applied to the washwater return line 105, and a hydrogen peroxide treatment zone 104, i.e., a hydrogen peroxide injection, within the second UV treatment 103. The first UV treatment 102 can be applied to an area below the washwater packing zone 101 by implementing, e.g., a collar 108 to illuminate the region above and/or below the washwater packing zone 101. The first and second UV treatments 102 and 103, i.e., the UV treatment zone, can be performed with, e.g., low pressure mercury lamps, and the first and second UV treatment 102 and 103 light can be emitted at about 254 nm for destroying and/or substantially destroying a first emission compound, e.g., nitrosamines, nitramines, or the like, above and/or below the washwater packing zone 101 and in the washwater return line 103. In addition, the first UV treatment 102 can be applied above and/or below the washwater packing zone 101. This generally enables transmittance of the UV light through both the water and gas phases, thereby permitting UV photolysis of gas phase compounds, e.g., nitrosamines, nitramines, and the like, as well. Further, at about 254 nm, nitrite and/or nitrate generally do not absorb UV light significantly, thus minimizing competition for photons. Medium pressure UV lamps may also be applied for this purpose. However, their emission spectra generally overlap those of nitrite and nitrate to a greater degree and may be less efficient. It should be understood that the first and second UV treatments 102 and 103 can destroy and/or substantially destroy a plurality of first emission compounds during their application above and/or below the washwater packing zone 101 and on the washwater return line 105.

a. UV and Hydrogen Peroxide Treatment Experimental Protocols and Results

Washwaters were generally collected from a pilot plant consisting of a carbon dioxide absorber column and a washwater scrubber and lacking a desorber column. The samples were collected after operation of the pilot plant with the following two model amine-based solvents in the absorber column: (i) about 35% of a monoethanolamine ("MEA")-based solvent and (ii) about 25% of a 2-amino-2-methyl-1-propanol ("AMP") and about 15% of a piperazine ("PZ") solution. The pilot washwater samples were collected after several days of operation. However, due to condensation of vapors from the absorber unit, the washwater volume generally accumulated. Typically, to maintain a constant volume, the excess volume was blown down, such that the average residence time of the washwater was about 10 hours. Based upon an assumed contact time of washwater with the exhaust gas within the washwater scrubber of about 2.2 minutes for each passage of the water, it was estimated that the accumulation of washwater constituents for each pass through the washwater scrubbing unit was about 0.37% of that observed in the raw washwater samples. This diluted sample approximated the concentrations of constituents that need to be treated continuously by the apparatus located in-line with the washwater recycle line, i.e., the washwater return line.

Specific and total N-nitrosamines and N-nitramines were measured in the washwaters. Table 1 below presents concentrations representing about 0.37% of the measured concentrations to indicate the concentrations of constituents anticipated to accumulate within the washwaters for each pass through the washwater scrubbing unit. It should be noted that 1-nitrosopiperazine is one of the few N-nitrosamines to exhibit low recoveries within the total N-nitrosamine assay, i.e., approximately 67%. Table 1 presents the raw total N-nitrosamine value for the diluted PZ/AMP-based washwater. Because 1-nitrosopiperazine is a major constituent of the total N-nitrosamines in the exemplary washwater, the actual total N-nitrosamine value for this washwater would need to be adjusted to account for the lower recovery for this specific N-nitrosamine constituent. Thus, the actual total N-nitrosamine can be approximately 320 nM.

TABLE 1

N-Nitrosamine and N-Nitramine Concentrations in Pilot Washwater Samples

| Washwater Constituents | Concentration (nM) |
| --- | --- |
| MEA-based washwater | |
| Total N-nitrosamine | 2.7 |
| N-nitrosodiethanolamine | 0.2 |
| N-nitrodiethanolamine | <0.02 |
| N-nitrosomorpholine | 0.00044 |
| N-nitrosopiperidine | 0.0022 |
| N-nitrosodimethylamine | 0.0020 |
| PZ/AMP-based washwater | |
| Total N-nitrosamine | 215 |
| 1-nitrosopiperazine | 237 |
| 1-nitropiperazine | <5.5 |
| 1,4-dinitrosopiperazine | 1.1 |
| 1-nitro-4-nitrosopiperazine | 0.011 |
| 1,4-dinitropiperazine | 0.1 |

In general, N-nitrosamines and N-nitramines are susceptible to direct photolytic destruction when exposed to UV light. The removal efficiency of N-nitrosamines and N-nitramines was characterized by first determining the quantum yields for destruction, i.e., Φ is equal to moles of compound destroyed/moles of photons, at about 254 nm of low pressure UV ("LP UV") and in deionized water buffered at a pH of about 10 with a borate buffer (Table 2 below). The quantum yields were determined in accordance with Equation 5 below, which is applicable to dilute aqueous solutions with a total solution absorbance of less than or equal to about 0.1 (see, e.g., Zepp, R. G., *Environ. Sci. Technol.*, 12, p. 327-329 (1978)).

$$-\frac{dC}{dt} = k_s * [C] = \frac{S}{V} * I(\lambda) * \Phi * 2.303 * \varepsilon * L * [C] \quad (5)$$

where $k_s$ is the photolysis rate constant ($s^{-1}$), [C] is the reactant or product being monitored (M), S is the surface area ($cm^2$), V is the volume of solution (L), I(λ) is the surface irradiance (moles of photons/$cm^2$/s or Einsteins/$cm^2$/s), Φ is the quantum yield (moles of compound destroyed/moles of photons), L is the path length (cm), and ε is the nitrosamine or nitramine molar adsorption coefficient ($M^{-1}$ $cm^{-1}$) listed in Table 2 below. The experiments generally employed a semi-collimated LP UV irradiation system with about a 500 mL open-top top cylindrical illumination dish. The illumination pathlength was determined to be about 4.1 cm, i.e., equivalent to the sample depth in the dish, using iodide-iodate (about 0.6 M KI and about 0.1 M $KIO_3$) actinometry. Use of the low absorbance equation was appropriate since the solution absorbance ($\alpha L$) was approximately 0.1 for a solution absorbance coefficient $\alpha$ of about 0.025 cm$^{-1}$. In order to determine the first order destruction rate constant $k_s$, the initial rates method was used, where solutions containing varying initial nitrosamine and/or nitramine doses from about 0 µM to about 1.5 µM and about 1.0 mM borate buffer at a pH of about 10 were irradiated at short time intervals (see, e.g., Levenspiel, O., *Chemical Reaction Engineering*, John Wiley & Sons, New York, p. 65-67 (1999)). The rate of compound loss (-dC/dt) was plotted against the compound concentration and the photolysis rate constant $k_s$ was equivalent to the slope of this linear relationship. Alternatively, decreasing concentrations of the nitrosamine and nitramine were monitored for increasing illumination times and fit to a first order decay model. Chemical actinometry was further utilized to determine the surface irradiance I. With the photolysis rate constant $k_s$ and surface irradiance I values, Equation 5 was rearranged to solve for the quantum yields. Thus, the quantum yields were determined to range from about 0.03 to about 0.28 at a pH of approximately 10 for the various nitrosamines and nitramines.

TABLE 2

Fluence Requirements for Specific N-Nitrosamines and N-Nitramines

| Compound | $\varepsilon_{254}$ (M$^{-1}$cm$^{-1}$) | $\Phi$ at pH 10 | Required Fluence (mJ/cm$^2$) |
| --- | --- | --- | --- |
| N-nitrosodimethylamine | 1,670 | 0.17 | 1674 |
| N-nitrodimethylamine | 4,570 | 0.21 | 502.3 |
| N-nitromonoethanolamine | 2,290 | 0.25 | 811.4 |
| N-nitrosodiethanolamine | 6,100 | 0.23 | 340.3 |
| N-nitrodiethanolamine | 6,800 | 0.10 | 703.2 |
| N-nitrosomorpholine | 4,850 | 0.04 | 2775.3 |
| N-nitromorpholine | 6,400 | 0.28 | 263.7 |
| 1-nitrosopiperazine | 3,900 | 0.03 | 4586.1 |
| 1-nitropiperazine | 6,070 | 0.10 | 753.4 |
| 1,4-dinitrosopiperazine | 8,700 | 0.16 | 329.6 |
| 1,4-dinitropiperazine | 13,900 | 0.12 | 277.6 |

Equation 5 was further solved and used to calculate the experimental time required to achieve about 90%, i.e., one log, removal of each nitrosamine and/or nitramine. UV treatment has been implemented for disinfection of drinking water. In particular, for drinking water treatment, the UV application rates are generally provided as "fluence" in units of mJ/cm$^2$. Fluence characterizes the cumulative energy applied to a solution for disinfection. To enable comparison of the energy requirements for destruction of about 90% of each nitrosamine and/or nitramine to those typically applied for drinking water disinfection, the experimental times required for about 90% removal were converted to cumulative surface irradiance (moles of photons/cm$^2$) using Equation 5. Additionally, for an LP UV system, the cumulative surface irradiance was converted to fluence (mJ/cm$^2$) by multiplying by the energy associated with photons of wavelength about 254 nm. With the exception of N-nitrosodimethylamine, N-nitrosomorpholine and 1-nitrosopiperazine, the fluence requirements ranged from about 264 to about 811 mJ/cm$^2$. Although these values are above the approximately 40 to 200 mJ/cm$^2$ typically applied for drinking water disinfection, they are generally within the range of fluence applied for Advanced Oxidation Process ("AOP") treatment of drinking waters and/or wastewaters. N-nitrosodimethylamine, N-nitrosomorpholine and 1-nitrosopiperazine required higher fluences due to either lower molar absorption coefficients or lower quantum yields. N-nitrosodimethylamine and N-nitrosomorpholine were minor constituents of the total nitrosamines in the MEA-based washwater sample as listed in Table 1. However, previous research indicated that dropping the solution pH to about 8 could increase the quantum yield for N-nitrosodimethylamine to approximately 0.3, thereby improving the process efficiency (see, e.g., Lee et al., *Environ. Sci. Technol.*, 39, p. 9702-9709 (2005)).

These calculations considered the individual compounds within buffered deionized water solutions. In authentic washwaters, absorption of UV photons by washwater constituents other than the target nitrosamines and/or nitramines can reduce the process efficiency. In addition, the hydrogen peroxide that can be added to promote the formation of radicals for the indirect photolytic destruction of other solution components, e.g., solvent amines and/or aldehydes, generally also absorbs UV light. For example, for the about 254 nm photons emitted by low pressure mercury lamps, the $\varepsilon_{H_2O_2}$ is equal to about 18.2 M$^{-1}$ cm$^{-1}$ and $\Phi$ is equal to about 0.5. However the absorbance coefficients of the two pilot plant washwater samples diluted to represent one passage through the washwater scrubbing unit were about 0.0017 cm$^{-1}$ for the MEA-based solvent and about 0.0031 cm$^{-1}$ for the PZ/AMP-based solvent. For the about 4.07 cm reactor path length employed in the experimental evaluations, the total solution absorbance ($\alpha L$) was less than about 0.1, even with an injection of about 40 mg/L of hydrogen peroxide. The about 40 mg/L of hydrogen peroxide concentration was selected since preliminary experiments indicated that this was an optimum concentration for degradation of amines in washwaters by radicals, e.g., hydroxyl radicals and/or associated carbonate radicals. However, it should be understood that alternative concentrations of hydrogen peroxide can be implemented, e.g., a range of about 10 mg/L to about 60 mg/L. Accordingly, no significant increase in applied fluence was generally needed to overcome the UV absorbance by matrix components.

Samples of the washwaters collected from the pilot plants were treated within the same semi-collimated beam apparatus generally without any dilution. Aliquots of the samples were removed during the illumination for measurement of total N-nitrosamines (see, e.g., Kulshrestha et al., *Environ. Sci. Technol.*, 44, p. 3369-3375 (2010)). Treatment of undiluted samples was necessary to ensure measureable total N-nitrosamine signals. The total solution absorbances of the MEA-based and PZ/AMP-based washwaters were about 0.67 cm$^{-1}$ and about 0.54 cm$^{-1}$, respectively. Because these values exceed 0.1, Equation 5 was not applicable. The total N-nitrosamine results were therefore analyzed in accordance with Equation 6 below, which is generally applicable (see, e.g., Zepp, R. G., *Environ. Sci. Technol.*, 12, p. 327-329 (1978)).

$$-\frac{dC}{dt} = k_s * [C] = \frac{S}{V} * I(\lambda) * (1 - 10^{-\alpha_\lambda 1}) * \frac{\sum (\varepsilon_\lambda \Phi)}{\alpha_\lambda} * [C] \qquad (6)$$

where $k_s$ is the observed total N-nitrosamine photolysis rate constant (s$^{-1}$), [C] is the total N-nitrosamine concentration being monitored (M), S is the surface area (cm$^2$), V is the volume of solution (L), I($\lambda$) is the surface irradiance (moles of photons/cm$^2$/s or Einsteins/cm$^2$/s), 1 is the path length (cm), $\alpha_\lambda$ is the total solution absorbance at wavelength $\lambda$, $\varepsilon_\lambda$ is the molar adsorption coefficient (M$^{-1}$ cm$^{-1}$) for an individual N-nitrosamine constituent of the total nitrosamine population and $\Phi$ is the quantum yield (moles of total N-nitrosamine destroyed/moles of photons) of that constituent. The experimental data were fit to Equation 6 to evaluate $\Sigma(\epsilon_\lambda \Phi)$ for each washwater, i.e., about 302.5 $M^{-1}$ $cm^{-1}$ for the total N-nitrosamines in the MEA-based washwater and about 1030 $M^{-1}$ $cm^{-1}$ for the total N-nitrosamines in the PZ-AMP-based washwater. For implementation of this technology, the washwater would be treated during each pass of the washwater through the scrubbing unit. Accordingly, the total solution absorbance would be lower, such that the conditions of Equation 5 would apply. The $\Sigma(\epsilon_\lambda \Phi)$ values were employed in Equation 5 to calculate fluence requirements needed for about 90% destruction of total N-nitrosamines, i.e., about 1558 $mJ/cm^2$ for the MEA-based washwater and about 458 $mJ/cm^2$ for the PZ/AMP-based washwater. It should be noted that as 1-nitrosopiperazine is a major constituent of the total N-nitrosamine signal for the PZ/AMP-based washwater, a higher fluence requirement was generally expected for about 90% removal of total N-nitrosamines in this washwater, i.e., see Table 2. The lower fluence requirements obtained from monitoring total N-nitrosamines generally implies that indirect photolysis of 1-nitrosopiperazine, i.e., formation of reactive intermediates from photolytic reactions with matrix constituents, may be significant for this washwater.

In general, a product of N-nitrosodimethylamine ("NDMA") photolysis, a model for N-nitrosamines, includes, e.g., methylamine, dimethylamine, nitrite, nitrate, or the like (see, e.g., Lee et al., *Environ. Sci. Technol.*, 39, p. 9702-9709 (2005)). The experimentations performed indicated that LP UV treatment of NDMA generally forms, e.g., dimethylamine (DMA), monomethylamine (MMA), nitrite, nitrate, and the like. These byproducts provide approximately 100% nitrogen mass balance between a pH from about 6 to about 8 and under saturated $O_2$ conditions. The sum of dimethylamine and monomethylamine can account for approximately 100% of the dimethylamine functional group in NDMA. Similarly, the sum of nitrite and nitrate can account for approximately 100% of the nitrosyl nitrogen in NDMA. Under nitrogen-saturated conditions, the sum of dimethylamine and monomethylamine can account for approximately 60% of the dimethylamine functional group in NDMA. Although the products accounting for the other approximately 40% of the dimethylamine functional group are unaccountable, the approximately 100% mass balance on the nitroso functional group indicates that neither nitramine or nitrosamine byproducts remain.

Figure 3A:
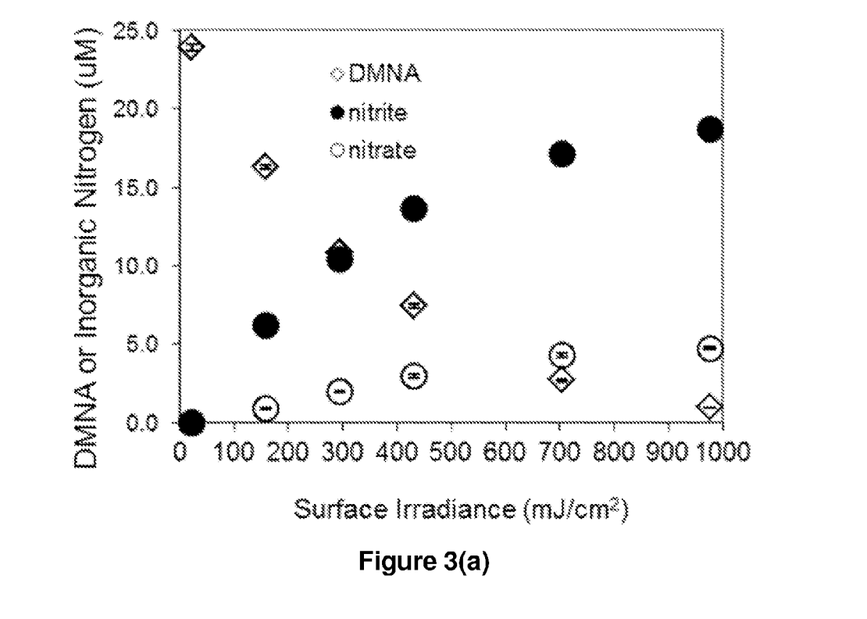
FIGS. 3(a) and (b) show the (a) nitrodimethylamine (DMNA) destruction as a function of UV dose and formation of nitrite and nitrate, and (b) formation of methylamine (MMA) and dimethylamine (DMA) byproducts following irradiation of DMNA with LP UV at pH 7.
Figure 3B:
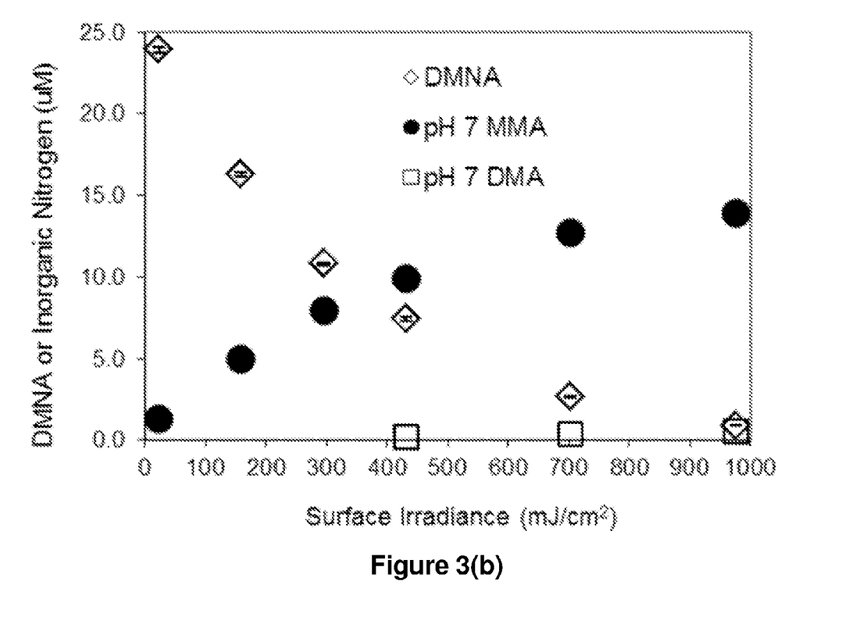

Additional experiments were conducted to characterize the products of the UV photolytic destruction of nitramines. In particular, the experiments were conducted using N-nitrodimethylamine, i.e., dimethylnitramine (DMNA), as a model for N-nitramines. The concentrations of MMA, DMA, nitrite and nitrate were monitored at a pH of about 7 under air-saturated conditions for the application of different LP UV surface irradiance (fluence) to about 25 $\mu M$ DMNA as can be seen in FIGS. 3(*a*) and (*b*). The sum of nitrite and nitrate accounted for approximately 100% of the nitro functional group in DMNA. In particular, the nitrite generally predominated by accounting for approximately 80% of this total. The sum of dimethylamine and monomethylamine accounted for approximately 56% of the dimethylamine functional group in DMNA. Although the products accounting for the other approximately 44% of the dimethylamine functional group are unaccountable, the approximately 100% mass balance on the nitro functional group indicates that neither nitramine or nitrosamine byproducts remain. Alternative and/or additional nitrosamines and/or nitramines relevant to carbon sequestration, e.g., 1-nitrosopiperazine, N-nitromorpholine, and the like, may also be destroyed and/or substantially destroyed by the first and second UV treatments 102 and 103 to form similar amine, nitrite and/or nitrate products.

The hydrogen peroxide treatment zone 104, i.e., the hydrogen peroxide injection, within the second UV treatment 103 on the washwater return line 105 generally produces radicals, e.g., hydroxyl radicals, carbonate radicals produced from hydroxyl radical reactions with carbonates, and the like. These radicals further generally oxidize and/or substantially oxidize, i.e., convert and/or substantially convert, a second emission compound, including a second emission compound formed by UV irradiation, to a less volatile final product and/or species, e.g., nitrite to nitrate, aldehyde to carboxylic acid, amine to carboxylic acid and nitrate, or the like. The experiments performed evaluated the loss of the MEA amine during LP UV irradiation in the presence of about 40 mg/L $H_2O_2$ of the pilot plant washwater sample associated with the MEA-based solvent diluted to represent one passage of the washwater through the scrubber unit. Table 3 below provides the concentrations of some of the specific constituents within the diluted pilot washwater sample. The ion chromatography system implemented did not resolve the acetate and formate peaks. The combined concentrations of acetate and formate were quantified against a standard curve constructed from equimolar formate and acetate stock solutions. Carbonate species concentrations were calculated based upon equilibration with carbon dioxide in the gas phase with the washwater solution at a pH of about 9.4, i.e., the pH of the diluted washwater. Since the washwater samples could have equilibrated with atmospheric carbon dioxide during shipment and storage, carbonate concentrations were calculated for equilibration of about a 25° C. washwater with the carbon dioxide in the atmosphere, i.e., about 0.04%. In addition to the carbonate species, MEA was the generally the predominant species.

TABLE 3

Concentrations of Constituents of the MEA-Based Washwater

| Washwater Constituents | Concentration | Units |
|---|---|---|
| Total N-nitrosamine | 2.7 | nM |
| N-nitrosodiethanolamine | 0.2 | nM |
| N-nitrodiethanolamine | <0.02 | nM |
| N-nitrosomorpholine | 0.00044 | nM |
| N-nitrosopiperidine | 0.0022 | nM |
| N-nitrosodimethylamine | 0.0020 | nM |
| Monoethanolamine (MEA) | 84 | µM |
| Nitrite | 767 | nM |
| Nitrate | 91 | nM |
| Formaldehyde | 730 | nM |
| Formate and acetate | 4015 | nM |
| Oxalate | 8.4 | nM |
| Carbonic acid | 13 | µM |
| Bicarbonate | 15 | mM |
| Carbonate | 1.8 | mM |
| Absorbance at 254 nm | 0.0017 | $cm^{-1}$ |

Figure 4:
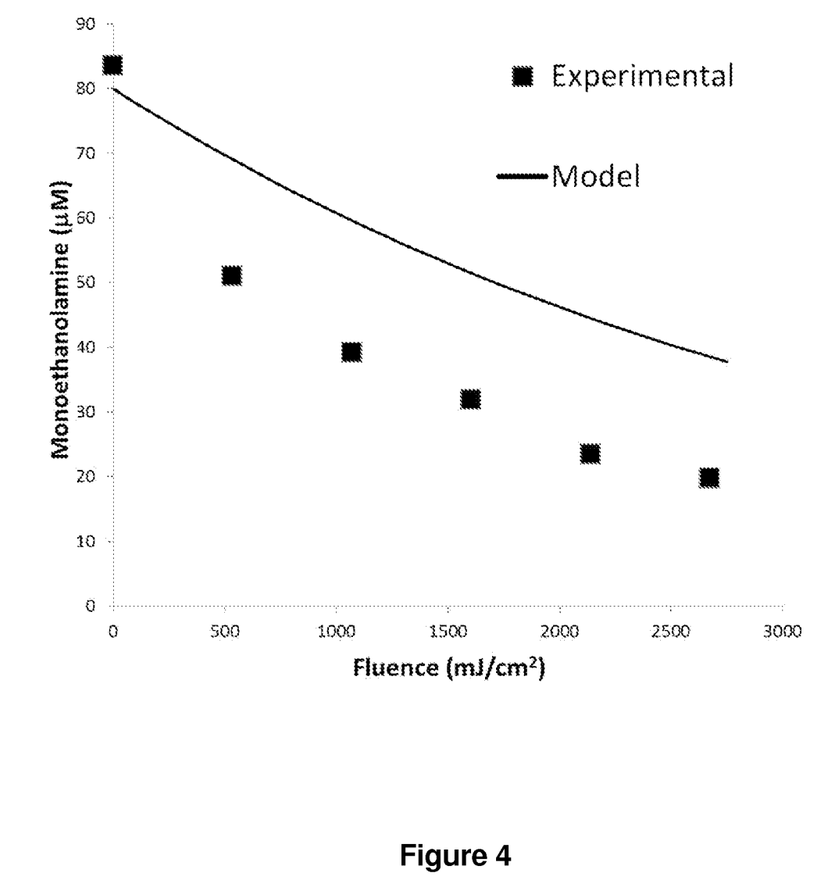
FIG. 4 shows the measured and modeled destruction of MEA versus LP UV influence in the presence of 40 mg/L hydrogen peroxide.

Turning to FIG. 4, the loss of MEA as a function of applied LP UV fluence is provided. In particular, the loss of MEA was approximately first order in MEA with an applied fluence of about 1000 $mJ/cm^2$ resulting in about a 50% loss of MEA. This fluence is within the range of fluence applied for Advanced Oxidation Process (AOP) treatment of drinking waters and wastewaters.

A kinetic model was constructed using Kintecus® modeling software. Table 4 below presents rate constants for some of the important reactions employed for the model.

FIG. 4 illustrates the model results using the initial species concentrations presented in Table 3, where formate and acetate were each assumed to account for about 50% of their combined total. It should be noted that the model generally under-predicts MEA destruction. For example, the MEA remaining after a fluence of about 2700 mJ/cm² was measured to be approximately 20 µM and was modeled to be approximately 38 µM. However, given the complexity of the model, the incomplete characterization of washwater constituents and the uncertainty in rate constants, e.g., the assumption that the rate constant for carbonate radical reaction with MEA is the same as for the reaction rate constant of carbonate radical with diethylamine, the model fit is adequate. The model further indicates that the carbonate radical concentration, i.e., $CO_3^{\cdot -}$, is about 3 orders of magnitude higher than the hydroxyl radical concentration, e.g., with $[CO_3^{\cdot -}]$ equal to about $2.7 \times 10^{-11}$ M and $[OH^{\cdot}]$ equal to about $4.3 \times 10^{-14}$ M at an approximately 1,000 mJ/cm² LP UV fluence. Accounting for the difference in rate constants for reactions of the two radicals with MEA, each radical is approximately of equal importance for MEA destruction. Modeling also indicates that a LP UV fluence of about 2,750 mJ/cm² in the presence of about 40 mg/L $H_2O_2$ would achieve approximately 75% removal of the initial about 767 nM of nitrite, approximately 60% removal of an assumed initial about 730 nM of acetaldehyde, and approximately 20% removal of the initial about 730 nM of formaldehyde. The lower removal of formaldehyde is typically related to its occurrence in the less reactive methanediol form.

TABLE 4

Rate Constants for Kinetic Model

| Compound | k $(M^{-1}s^{-1})$ | Reference |
|---|---|---|
| Hydoxyl radical reactions | | |
| Monoethanolamine | $2.90 \times 10^9$ | 1 |
| Monoethanolamine-H$^{+a}$ | $3.00 \times 10^8$ | 1 |
| Acetaldehyde | $3.60 \times 10^9$ | 2 |
| Hydrated formaldehyde $(CH_2(OH)_2)^b$ | $8.10 \times 10^8$ | 3 |
| Nitrite | $1.00 \times 10^{10}$ | 4 |
| Bicarbonate | $8.50 \times 10^6$ | 5 |
| Carbonate | $3.90 \times 10^8$ | 5 |
| Formate | $3.20 \times 10^9$ | 6 |
| Acetate | $8.50 \times 10^7$ | 7 |
| Oxalate | $7.70 \times 10^6$ | 8 |
| Carbonate radical reactions | | |
| Nitrite | $6.60 \times 10^5$ | 9 |
| Formate | $1.50 \times 10^5$ | 10 |
| Acetate | $6.00 \times 10^2$ | 11 |
| Monoethanolamine$^c$ | $3.80 \times 10^6$ | 12 |

$^a$Protonated MEA.
$^b$In water, formaldehyde is more stable in its hydrated form $(CH_2(OH)_2)$ where $K_{eq} = 1.59 \times 10^3$ (Reference 13).
$^c$Using the rate constant for diethylamine.
1 Kishore, K. et al., *Res. Chem. Intermed.*, 31, p. 875-884 (2005).
2 Schuchmann, M. N., *J. Am. Chem. Soc.*, 110, p. 5698-5701 (1988).
3 Chin, M. et al., *Aquatic and Surface Photochemistry*, CRC Press, Boca Raton, p. 85-96 (1994).
4 Mack, J. et al., *J. Photochem. Photobio.*, 128, p. 1-13 (1999).
5 Crittenden, J. C. et al., *Water Research*, 33, p. 2315-2328 (1999).
6 Motohashi, N. et al., *Chem. Pharm. Bull.*, 41, p. 1842-1845 (1993).
7 Willson, R. L. et al., *Int. J. Radiat. Phys. Chem.*, 3, p. 211-220 (1971).
8 Getoff, N. et al., *J. Phys. Chem.*, 75, p. 749-755 (1971).
9 Huie, R. E. et al., *Int. J. Chem. Kinet.*, 23, p. 541-552 (1991).
10 Draganic, Z. D. et al., *Radiat. Phys. Chem.*, 38, p. 317-321 (1991).
11 Kuz'min, V. A., *High Energy Chem.*, 6, p. 338-339 (1972).
12 Elango, T. P. et al., *Tetrahedron*, 41, p. 3837-3843 (1985).
13. Winkelman, J. G. M. et al., *Chem. Eng. Sci.*, 57, p. 4067-4076 (2002).

To estimate carbonate species concentrations within a washwater unit servicing a coal-fired power plant, carbonate concentrations were also calculated for equilibration with approximately 1% carbon dioxide in about 40° C. washwater, reflecting approximately 90% carbon dioxide removal from the approximately 10% carbon dioxide in coal-fired power plant exhaust by an amine-based carbon capture absorber unit. The model results indicate that the higher carbonate concentrations generally reduce the efficiency of MEA destruction by promoting the formation of the less reactive carbonate radical by carbonate scavenging of hydroxyl radicals. For example, the modeled concentration of MEA remaining after a LP UV fluence of approximately 2,740 mJ/cm² in the presence of about 40 mg/L $H_2O_2$ was about 52 µM, compared with about 38 µM at the lower carbon dioxide exposure.

2. UV and Ozonation Treatment

With reference to FIG. 2(*b*), an alternative exemplary apparatus or system 100' is provided. In particular, the exemplary apparatus or system 100' of FIG. 2(*b*) generally includes a chamber 107' defining at least one washwater packing zone 101' positioned therewithin. The chamber 107' can be, e.g., a pipeline, and the like. The exemplary apparatus 100' further includes a first UV treatment 102' applied to an area below the washwater packing zone 101', a washwater return line 105', a second UV treatment 103', e.g., a UV illumination system, applied to the washwater return line 105', and an ozonation treatment zone 104', i.e., an ozone injection, downstream of the second UV treatment 103'. The first UV treatment 102' can be applied to an area below the washwater packing zone 101' by implementing, e.g., a collar 108' to illuminate the region above and/or below the washwater packing zone 101'. The first and second UV treatments 102' and 103', i.e., the UV treatment zone, can be performed with, e.g., low pressure mercury lamps, and the first and second UV treatment 102' and 103' lights can be emitted at about 254 nm for destroying and/or substantially destroying a first emission compound, e.g., nitrosamines, nitramines, or the like, below and/or above the washwater packing zone 101' and in the washwater return line 103'. In addition, the first UV treatment 102' can be applied above and/or below the washwater packing zone 101'. This generally enables transmittance of the UV light through both the water and gas phases, thereby permitting UV photolysis of gas phase compounds, e.g., nitrosamines, nitramines, and the like, as well. Further, at about 254 nm, nitrite and/or nitrate generally do not absorb UV light significantly, thus minimizing competition for photons. It should be understood that the first and second UV treatments 102' and 103' can destroy and/or substantially destroy a plurality of first emission compounds during their application above and/or below the washwater packing zone 101' and on the washwater return line 105', as was discussed above.

The ozonation treatment zone 104', i.e., an ozone injection, of the exemplary apparatus 100' depicted in FIG. 2(*b*) can generally be applied to the washwater return line 105'. The ozonation treatment zone 104' further generally receives an ozonation medium sufficient to oxidize and/or substantially oxidize, i.e., convert and/or substantially convert, a second emission compound, including a second emission compound formed by UV irradiation, to a less volatile final product and/or species, e.g., nitrite to nitrate, aldehyde to carboxylic acid, amine to carboxylic acid and nitrate, or the like. It should be understood that the ozonation treatment zone 104' can oxidize and/or substantially oxidize a plurality of second emission compounds when applied to the washwater return line 105'. In general, the destruction of aldehydes and nitrite may inhibit and/or substantially inhibit nitrosamine formation within the washwater packing zone 101' and/or washwater return line 105'.

Table 5 below provides ozonation reaction rate constants for relevant species and/or compounds. Although the reaction rate constants for MEA and diethanolamine are not readily available, the reaction rate constant values for, e.g., ethanol, diethylamine and butylamine, indicate that the amine group would be a significant target for reaction. For drinking water disinfection, application of approximately 5 mg/L ozone (about 100 µM) is relevant. Implementing about $3.7 \times 10^5$ $M^{-1}$ $s^{-1}$, i.e., the average of the rate constants for reaction of ozone with diethylamine and butylamine, to estimate the rate constant for reaction of ozone with MEA, the application of approximately 50 mg/L ozone (about 1 mM) can achieve MEA destruction over timescales of less than about 1 second. Similarly, destruction of acetaldehyde can occur over timescales of approximately 10 minutes. It should be noted that ozone generally self-decays at high pH levels, thereby generating hydroxyl radicals that participate in the destruction, e.g., control and/or treatment, of washwater contaminants, yielding similar products (Table 4). In addition, placement and/or application of the ozone injection point, e.g., the ozonation treatment zone 104', at the beginning of the washwater return line 105' generally minimizes ozone loss in the exhaust gas. Thus, the first and second UV treatments 102' and 103', combined with the ozonation treatment zone 104', can destroy and/or substantially destroy contaminants of concern and maintain a low, steady-state concentration.

a. UV and Ozonation Treatment Experimental Protocols and Results

Figure 5:
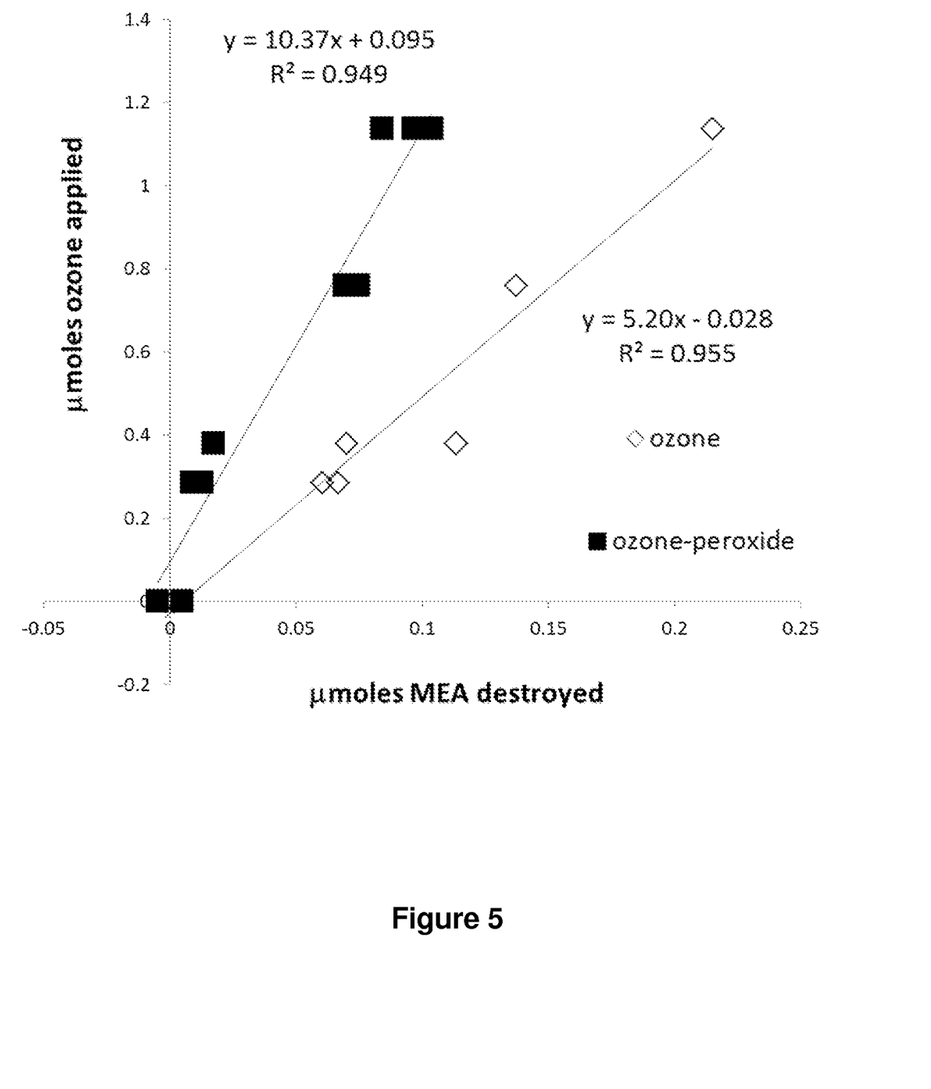
FIG. 5 shows applied moles of ozone applied versus moles of monoethanolamine destroyed within a diluted MEA-based washwater from a pilot plant with and without a one-to-one mole ratio of ozone to hydrogen peroxide.

An experiment was conducted in which the diluted MEA-based washwater was dosed under headspace-free conditions at approximately room temperature with different concentrations of an ozone stock solution generated by bubbling ozone through deionized water. The reactions were allowed to proceed overnight in the dark. Samples were analyzed for residual monoethanolamine. FIG. 5 is a plot of the µmoles of ozone applied against the µmoles of ozone destroyed. The results generally indicate that the required molar ratio of ozone to monoethanolamine is about 5.2 to achieve monoethanolamine destruction in the diluted MBA-based washwater. Although monoethanolamine is generally one of the main washwater constituents (Table 3), this mole ratio is not necessarily the reaction stoichiometry for ozone destruction of monoethanolamine. Rather it is an observed stoichiometry that accounts for side reactions including ozone destruction at high pH and ozone reactions with other solution constituents. The reaction kinetics are generally anticipated to be rapid as discussed previously. For a washwater accumulating about 84 µM monoethanolamine for each pass through the washwater scrubber (Table 3), these results generally indicate that an ozone dosage of about 20 mg/L would be required for monoethanolamine removal. It should be noted that this concentration is about 5 times higher than those typically applied for water disinfection.

TABLE 5

Rate Constants for Ozone Reactions

| Compound | k ($M^{-1}s^{-1}$) | Reference |
|---|---|---|
| Ethanol | 0.37 | 1 |
| Diethylamine[a] | $6.2 \times 10^5$ | 2 |
| Butylamine[a] | $1.2 \times 10^5$ | 2 |
| Acetaldehyde | 1.5 | 3 |
| Nitrite | $3.7 \times 10^5$ | 1 |

[a]Unprotonated amines. Protonated amines are not reactive.
1 Von Gunten, U., *Water Research*, (2003).
2 Pryor, W. A. et al., *J. Am. Chem. Soc.*, 106, p. 7094-7100 (1984).
3 Schuchmann, M. N., *J. Am. Chem. Soc.*, 110, p. 5698-5701 (1988).

3. UV, Ozonation and Hydrogen Peroxide Treatment

With reference to FIG. 2(*c*), an alternative exemplary apparatus or system 100" is provided, generally including a chamber 107" defining at least one washwater packing zone 101" positioned therewithin. The chamber 107" can be, e.g., a pipeline, and the like. The exemplary apparatus or system 100" further includes a first UV treatment 102" applied to an area below the washwater packing zone 101", a washwater return line 105", a second UV treatment 103", e.g., a UV illumination system, applied to the washwater return line 105", an ozonation treatment zone 104", i.e., an ozone injection, applied to the washwater return line 105" and a hydrogen peroxide treatment zone 106", i.e., a hydrogen peroxide injection, within the ozonation treatment zone 104". In particular, the ozonation treatment zone 104" and the hydrogen peroxide treatment zone 106" can be coupled together to be applied to the washwater return line 105" downstream of the second UV treatment 102". In addition, the fast UV treatment 102" can be applied to an area below the washwater packing zone 101" by implementing, e.g., a collar 108" to illuminate the region above and/or below the washwater packing zone 101".

The first and second UV treatments 102" and 103", i.e., the UV treatment zone, can be performed with, e.g., low pressure mercury lamps, and the first and second UV treatment 102" and 103" lights can be emitted at about 254 nm for destroying and/or substantially destroying a first emission compound, e.g., nitrosamines, nitramines, or the like, below and/or above the washwater packing zone 101" and in the washwater return line 105". In addition, the first UV treatment 102" can be applied above and/or below the washwater packing zone 101". This generally enables transmittance of the UV light through both the water and gas phases, thereby permitting UV photolysis of gas phase compounds, e.g., nitrosamines, nitramines, and the like, as well. Further, at about 254 nm, nitrite and/or nitrate generally do not absorb UV light significantly, thus minimizing competition for photons. It should be understood that the first and second UV treatments 102" and 103" can generally destroy and/or substantially destroy a plurality of first emission compounds during their application above and/or below the washwater packing zone 101" and on the washwater return line 105", as discussed previously.

The ozonation treatment zone 104" of the exemplary apparatus 100" depicted in FIG. 2(*c*) can generally be applied to the washwater return line 105". The ozonation treatment zone 104" further generally receives sufficient ozonation medium sufficient to oxidize and/or substantially oxidize, i.e., convert and/or substantially convert, a second emission compound, including a second emission compound formed by UV irradiation, to a less volatile final product and/or species, e.g., nitrite to nitrate, aldehyde to carboxylic acid, amine to carboxylic acid and nitrate, or the like. It should be understood that the ozonation treatment zone 104"

can oxidize and/or substantially oxidize a plurality of second emission compounds when applied to the washwater return line 105". In general, the destruction of aldehydes and nitrite may inhibit and/or substantially inhibit nitrosamine formation within the washwater packing zone 101" and/or washwater return line 105", as discussed above.

The ozonation treatment zone 104", i.e., an ozone injection, together with the hydrogen peroxide treatment zone 106", i.e., a hydrogen peroxide injection, generally promote the formation of hydroxyl radicals. These radicals, along with others formed from hydroxyl radical reactions, e.g., carbonate radicals, further generally oxidize and/or substantially oxidize, i.e., convert and/or substantially convert, a second emission compound, including a second emission compound formed by UV irradiation, to a less volatile final product and/or species, e.g., nitrite to nitrate, aldehyde to carboxylic acid, amine to carboxylic acid and nitrate, or the like. It should be understood that the ozonation treatment zone 104" can oxidize and/or substantially oxidize a plurality of second emission compounds when applied to the washwater return line 105". In general, the destruction of aldehydes and nitrite may inhibit and/or substantially inhibit nitrosamine formation within the washwater packing zone 101" and/or washwater return line 105", as discussed previously.

a. UV, Ozonation and Hydrogen Peroxide Treatment Experimental Protocols and Results An experiment was conducted in which the diluted MEA-based washwater was dosed under headspace-free conditions at about room temperature with different concentrations of an ozone stock solution generated by bubbling ozone through deionized water. Prior to ozone injection, solutions were spiked with hydrogen peroxide to achieve an approximately 1:1 mole ratio with respect to the ozone being applied. The reactions were allowed to proceed overnight in the dark. Samples were analyzed for residual monoethanolamine. FIG. 5 plots the μmoles of ozone applied against the μmoles of ozone destroyed. The results indicate that the required molar ratio of ozone to monoethanolamine is about 10.4 to achieve monoethanolamine destruction in the diluted MEA-based washwater. Although monoethanolamine is generally one of the main washwater constituents (Table 3), this mole ratio is not necessarily the reaction stoichiometry for ozone destruction of monoethanolamine. Rather, it is an observed stoichiometry that accounts for side reactions including ozone destruction at high pH and ozone reactions with other solution constituents. The addition of hydrogen peroxide promotes hydroxyl radical destruction through ozone reactions with hydrogen peroxide (see Katsoyiannis et al., *Water Research*, 45, p. 3811-3822 (2011)). Hydroxyl radicals react rapidly with a wide range of compounds (Table 4), but are less selective oxidants than ozone (see von Gunten, *Water Research*, 37, p. 1443-1467 (2003)). The introduction of hydrogen peroxide approximately doubled the ozone dosage requirements to achieve monoethanolamine destruction compared to addition of ozone alone, as previously discussed. These results suggest that the direct ozone reaction with monoethanolamine is generally more effective at destroying monoethanolamine than reactions with hydroxyl radicals, potentially due to greater selective targeting of monoethanolamine with ozone. The reaction kinetics are generally anticipated to be rapid, as discussed previously. The addition of hydrogen peroxide may be beneficial as the promotion of hydroxyl radicals may enhance the degradation of aldehydes since the rate constants for hydroxyl radical reactions with aldehydes are about 8 orders of magnitude higher than for direct ozone reactions with aldehydes (Tables 4 and 5). Based on the target contaminants of concern, either exemplary configuration may be desirable.

Although the present disclosure has been described with reference to exemplary embodiments and implementations, it is to be understood that the present disclosure is neither limited by nor restricted to such exemplary embodiments and/or implementations. Rather, the present disclosure is susceptible to various modifications, enhancements and variations without departing from the spirit or scope of the present disclosure. Indeed, the present disclosure expressly encompasses such modifications, enhancements and variations as will be readily apparent to persons skilled in the art from the disclosure herein contained.

The invention claimed is:

1. A method for controlling emissions of carbon capture facilities, comprising:
   providing at least one washwater packing zone, a UV treatment zone positioned below and in fluid communication with the at least one washwater packing zone, and at least one washwater return line in fluid communication with the UV treatment zone;
   applying a UV treatment to a washwater stream in the UV treatment zone; and
   applying an ozonation treatment to the washwater stream in the at least one washwater return line;
   wherein the UV treatment substantially destroys a first emission compound in the washwater stream; and
   wherein the ozonation treatment substantially oxidizes a second emission compound in the washwater stream to a less volatile final product.

2. The method of claim 1, further comprising applying a second UV treatment to the wastewater stream in the at least one washwater return line.

3. The method of claim 1, wherein the ozonation treatment comprises applying an ozone injection to the washwater stream in the at least one washwater return line.

4. The method of claim 1, further comprising applying a hydrogen peroxide treatment within the ozonation treatment.

5. The method of claim 4, wherein the hydrogen peroxide treatment is a hydrogen peroxide injection.

6. The method of claim 4, wherein the hydrogen peroxide treatment substantially oxidizes the second emission compound to the less volatile final product.

7. The method of claim 1, wherein the first emission compound includes at least one of a nitrosamine and a nitramine.

8. The method of claim 1, wherein the second emission compound includes at least one of a nitrite, an aldehyde and an amine.

9. The method of claim 1, wherein the less volatile final product includes at least one of a nitrate, a carboxylic acid and an oxidized amine product.

10. The method of claim 2, wherein the UV treatment and the second UV treatment are applied in at least one of a water phase and a gas phase.

* * * * *